(12) United States Patent
Lau et al.

(10) Patent No.: US 9,156,871 B2
(45) Date of Patent: Oct. 13, 2015

(54) MATERIALS AND METHODS FOR PREVENTION AND TREATMENT OF VIRAL INFECTIONS

(71) Applicants: PURAPHARM COMPANY LIMITED, Hong Kong (CN); VERSITECH LIMITED, Hong Kong (CN)

(72) Inventors: Allan Sik Yin Lau, Hong Kong (CN); Lai Hung Cindy Yang, Hong Kong (CN)

(73) Assignees: BAGI RESEARCH LIMITED, Hong Kong (CN); VERSITECH LIMITED, Hong Kong (CN)

( * ) Notice: Subject to any disclaimer, the term of this patent is extended or adjusted under 35 U.S.C. 154(b) by 0 days.

(21) Appl. No.: 13/863,781

(22) Filed: Apr. 16, 2013

(65) Prior Publication Data

US 2013/0281393 A1    Oct. 24, 2013

Related U.S. Application Data

(60) Provisional application No. 61/636,184, filed on Apr. 20, 2012.

(51) Int. Cl.
| | |
|---|---|
| *A61K 31/70* | (2006.01) |
| *A61K 31/7012* | (2006.01) |
| *A61K 31/7042* | (2006.01) |
| *C07H 15/18* | (2006.01) |
| *C07D 309/10* | (2006.01) |
| *C07H 15/26* | (2006.01) |

(52) U.S. Cl.
CPC .............. *C07H 15/18* (2013.01); *A61K 31/70* (2013.01); *A61K 31/7012* (2013.01); *A61K 31/7042* (2013.01); *C07D 309/10* (2013.01); *C07H 15/26* (2013.01)

(58) Field of Classification Search
None
See application file for complete search history.

(56) References Cited

U.S. PATENT DOCUMENTS

2007/0004011 A1* 1/2007 Dal Monte et al. ............. 435/74
2008/0261896 A1   10/2008 Tanaka et al.

FOREIGN PATENT DOCUMENTS

| CN | 1424318 A | 6/2003 |
|---|---|---|
| CN | 102304156 A | 1/2012 |
| EP | 1 736 166 B1 | 9/2008 |

OTHER PUBLICATIONS

Lopez et al., J. Org. Chem, 1994, vol. 59(4), 737-745.*
Duan et al., Journal of Asian Natural Products Research, Mar. 2012, vol. 14(3), 286-292.*
Awe et al., Phytomedicine, vol. 15, 2008, 301-305.*
Awe, E.O. et al., "Antinociceptive effect of *Russelia equisetiformis* leave extracts: Identification of its active constituents," *Phytomedicine*, 2008, vol. 18, p. 301-305.
Duan, Y.H. et al., "A new phenylpropanoid glucoside from the aerial parts of *Lygodium japonicum*,"*Journal of Asian Natural Products Research*, 2012, vol. 14, No. 3, p. 286-292.
Jennings, H.J., "Synthesis of 6-O-α and β-$_D$-xylopyranosyl-$_D$-mannopyranose. (Glycosidation of α- and β-$_D$-xylopyranosyl chloride 2, 3, 4-tri(chlorosulfate))," *Canadian Journal of Chemistry*, 1968, vol. 46, p. 2799-2805.
Lai, Y.C. et al., "A comprehensive investigation of anti-inflammatory diarylheptanoids from the leaves of *Alnus formosana*," *Phytochemistry*, 2012, vol. 73, p. 84-94.
Li, Q. et al., "Total synthesis of syringalide B, a phenylpropanoid glycoside," *Carbohydrate Research*, 2005, vol. 340, p. 1601-1604.
López, R. et al., "Enzymatic β-Galactosidation of Modified Monosaccharides: Study of the Enzyme Selectivity for the Acceptor and Its Application to the Synthesis of Disaccharides," *Journal of Organic Chemistry*, 1994, vol. 59, p. 737-745.
Wada, H. et al., "Chemical and Chemotaxonomical Studies of Ferns. LXXXVII. Constituents of *Trichomanes reniforme*," *Chemical & Pharmaceutical Bulletin*, 1995, vol. 43, No. 3, p. 461-465.
Zhang, S.Q. et al., "Total synthesis of the phenylpropanoid glycoside, grayanoside A," *Carbohydrate Research*, 1997, vol. 299, p. 281-285.

* cited by examiner

*Primary Examiner* — Traviss C McIntosh, III
(74) *Attorney, Agent, or Firm* — Saliwanchik, Lloyd & Eisenschenk

(57) ABSTRACT

The present invention provides novel and advantageous materials and methods for preventing and treating viral infection.

2 Claims, No Drawings

MATERIALS AND METHODS FOR PREVENTION AND TREATMENT OF VIRAL INFECTIONS

CROSS-REFERENCE TO A RELATED APPLICATION

This application claims the benefit of U.S. provisional application Ser. No. 61/636,184, filed Apr. 20, 2012, which is incorporated herein by reference in its entirety.

BACKGROUND OF THE INVENTION

Viral infections are responsible for many acute and chronic life-threatening diseases. It is estimated that about 33.4 million people are living with human immunodeficiency virus (HIV) worldwide. In addition, an estimated 2 billion people have been infected with hepatitis B virus, and 600,000 people die each year due to the acute or chronic consequences of the infection. Influenza is one of the most widely spread viral infections worldwide. Major influenza A pandemics include the Asian flu pandemic in 1957 (H2N2), the Hong Kong flu pandemic in 1968 (H3N2), the re-emergence of H1N1 (Russian flu) in 1970, the H5N1 bird flu in 1997 and 2003, and the outbreak of the swine flu (H1N1) in April 2009.

Despite extensive efforts, the development of effective anti-viral drugs has largely been empirical. Further, as virus strains change over time, the emergence of resistant mutants further diminishes the efficacy of existing anti-viral agents. Therefore, the development of additional novel anti-viral therapeutics is needed.

BRIEF SUMMARY OF THE INVENTION

The present invention provides novel and advantageous materials and methods for preventing and/or treating viral infection.

In one embodiment, the present invention provides compounds of formula I, having the following structure:

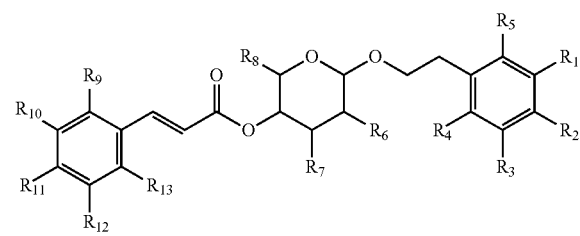

wherein $R_1$-$R_{13}$ are, independently —H, —OH, acyl, halo, haloalkyl, amino, alkylamino, hydroxyl, alkyl, hydroxylalkyl, alkoxy, thiol, cyano or —COOH.

In a specific embodiment, the compound of formula I is:

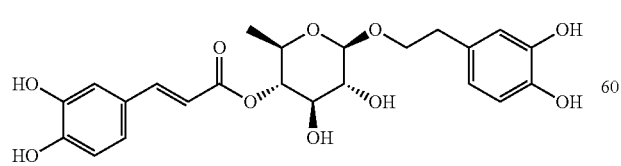

(E)-(2R,3S,4R,5R,6R)-6-(3,4-dihydroxyphenethoxy)-4,5-dihydroxy-2-methyltetrahydro-2H-pyran-3-yl 3-(3,4-dihydroxyphenyl)acrylate.

In one embodiment, the present invention provides compounds of formula II, having the following structure:

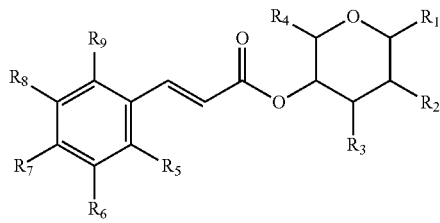

wherein $R_1$-$R_9$ are, independently —H, —OH, acyl, halo, haloalkyl, amino, alkylamino, hydroxyl, alkyl, hydroxylalkyl, alkoxy, thiol, cyano or —COOH.

In a specific embodiment, the compound of formula II is:

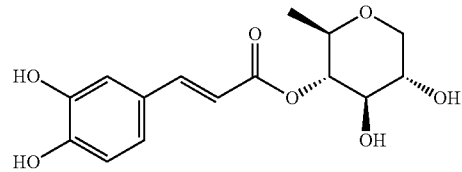 [SMILES: C[C@H]1OC[C@H](O)[C@@H](O)[C@@H]1OC(=O)/C=C/c1ccc(O)c(O)c1]

(E)-(2R,3S,4R,5S)-4,5-dihydroxy-2-methyltetrahydro-2H-pyran-3-yl 3-(3,4-dihydroxyphenyl)acrylate.

In one embodiment, the present invention provides compounds of formula III, having the following structure:

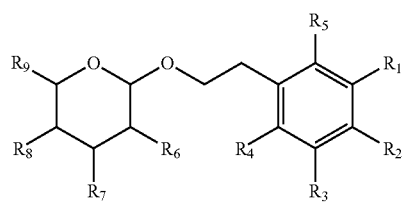

wherein $R_1$-$R_9$ are, independently —H, —OH, acyl, halo, haloalkyl, amino, alkylamino, hydroxyl, alkyl, hydroxylalkyl, alkoxy, thiol, cyano or —COOH.

In a specific embodiment, the compound of formula III is:

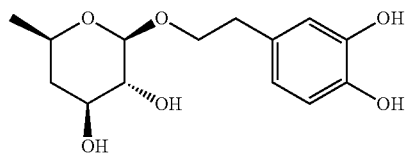 [SMILES: C[C@@H]1C[C@H](O)[C@@H](O)[C@H](OCCc2ccc(O)c(O)c2)O1]

(2R,3R,4S,6R)-2-(3,4-dihydroxyphenethoxy)-6-methyltetrahydro-2H-pyran-3,4-diol.

In one embodiment, the present invention provides compounds of formula IV, having the following structure:

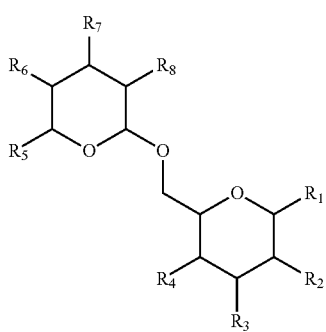

wherein $R_1$-$R_8$ are, independently —H, —OH, acyl, halo, haloalkyl, amino, alkylamino, hydroxyl, alkyl, hydroxylalkyl, alkoxy, thiol, cyano or —COOH.

In a specific embodiment, the compound of formula IV is:

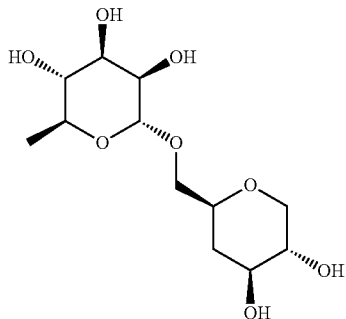 [SMILES: C[C@@H]1O[C@@H](OC[C@@H]2C[C@H](O)[C@@H](O)CO2)[C@H](O)[C@H](O)[C@H]1O]

(2R,3R,4R,5R,6S)-2-(((2S,4S,5S)-4,5-dihydroxytetrahydro-2H-pyran-2-yl)methoxy)-6-methyltetrahydro-2H-pyran-3,4,5-triol.

The present invention also provides therapeutic compositions, comprising an isolated or substantially pure compound selected from formula I to formula IV, or a salt thereof, and optionally, a pharmaceutically acceptable carrier. Also provided are uses of the compounds and compositions of the present invention for prevention and/or treatment of viral infection.

DETAILED DESCRIPTION OF THE INVENTION

The present invention provides novel and advantageous materials and methods for preventing and/or treating viral infection in a subject. Preferably, the compounds and compositions of the present invention are formulated for oral administration.

In one aspect, the present invention provides compounds having a chemical structure represented by formula I to formula IV.

In one embodiment, the present invention provides compounds of formula I, having the following structure:

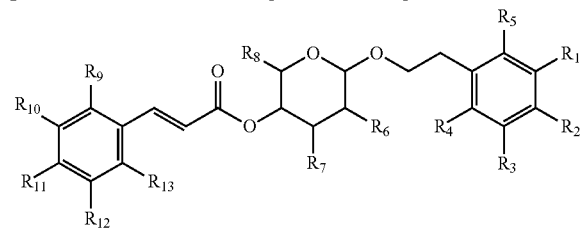

wherein $R_1$-$R_{13}$ are, independently —H, —OH, acyl, halo, haloalkyl, amino, alkylamino, hydroxyl, alkyl, hydroxylalkyl, alkoxy, thiol, cyano or —COOH.

In certain embodiments, one or more of $R_1$-$R_{13}$ of formula I are selected from —H, —OH, —$CH_3$, or —$OCH_3$.

In a specific embodiment, the compound of formula I is:

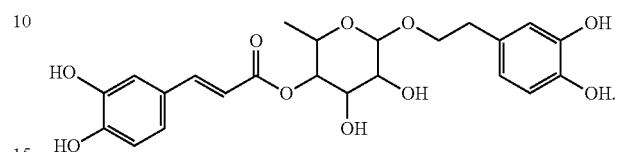

In a further specific embodiment, the compound of formula I is:

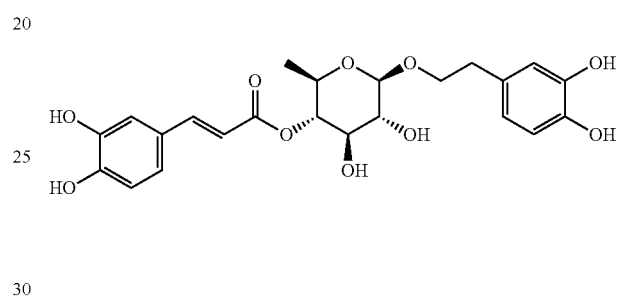

(E)-(2R,3S,4R,5R,6R)-6-(3,4-dihydroxyphenethoxy)-4,5-dihydroxy-2-methyltetrahydro-2H-pyran-3-yl 3-(3,4-dihydroxyphenyl)acrylate.

In one embodiment, the present invention provides compounds of formula II, having the following structure:

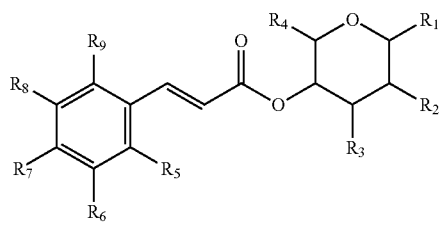

wherein $R_1$-$R_9$ are, independently —H, —OH, acyl, halo, haloalkyl, amino, alkylamino, hydroxyl, alkyl, hydroxylalkyl, alkoxy, thiol, cyano or —COOH.

In certain embodiments, one or more of $R_1$-$R_9$ of formula II are selected from —H, —OH, —$CH_3$, or —$OCH_3$.

In a specific embodiment, the compound of formula II is:

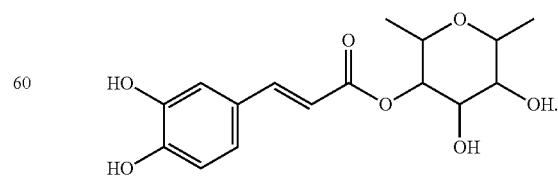

In a further specific embodiment, the compound of formula II is:

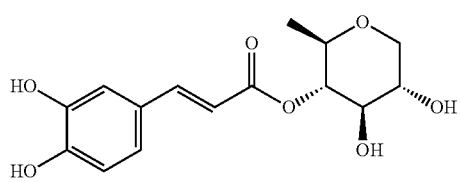

(E)-(2R,3S,4R,5S)-4,5-dihydroxy-2-methyltetrahydro-2H-pyran-3-yl 3-(3,4-dihydroxyphenyl)acrylate.

In one embodiment, the present invention provides compounds of formula III, having the following structure:

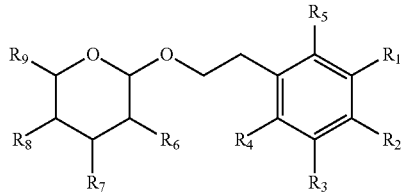

wherein $R_1$-$R_9$ are, independently —H, —OH, acyl, halo, haloalkyl, amino, alkylamino, hydroxyl, alkyl, hydroxyalkyl, alkoxy, thiol, cyano or —COOH.

In certain embodiments, one or more of $R_1$-$R_9$ of formula III are selected from —H, —OH, —$CH_3$, or —$OCH_3$.

In a specific embodiment, the compound of formula III is:

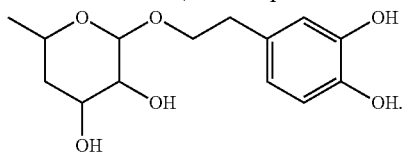

In a further specific embodiment, the compound of formula III is:

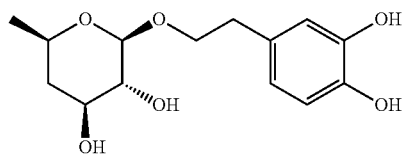 [SMILES: C[C@@H]1C[C@H](O)[C@@H](O)[C@H](OCCc2ccc(O)c(O)c2)O1]

(2R,3R,4S,6R)-2-(3,4-dihydroxyphenethoxy)-6-methyltetrahydro-2H-pyran-3,4-diol.

In one embodiment, the present invention provides compounds of formula IV, having the following structure:

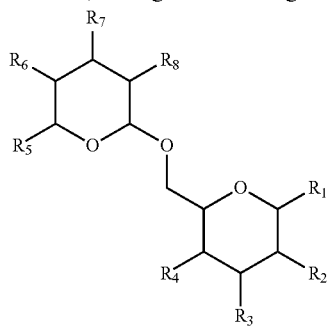

wherein $R_1$-$R_8$ are, independently —H, —OH, acyl, halo, haloalkyl, amino, alkylamino, hydroxyl, alkyl, hydroxyalkyl, alkoxy, thiol, cyano or —COOH.

In certain embodiments, one or more of $R_1$-$R_8$ of formula IV are selected from —H, —OH, —$CH_3$, or —$OCH_3$.

In a specific embodiment, the compound of formula IV is:

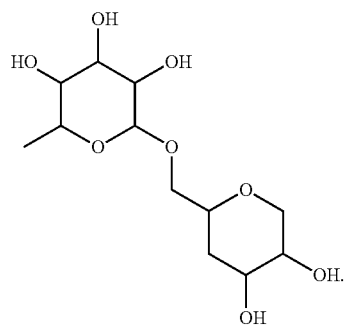 [SMILES: CC1OC(OCC2CC(O)C(O)CO2)C(O)C(O)C1O]

In a further specific embodiment, the compound of formula IV is:

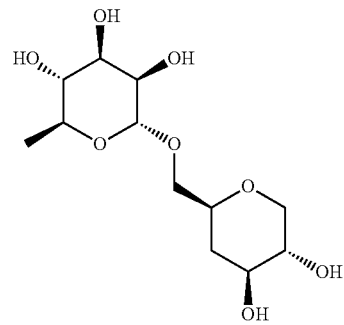 [SMILES: C[C@@H]1O[C@@H](OC[C@@H]2C[C@H](O)[C@@H](O)CO2)[C@H](O)[C@H](O)[C@H]1O]

(2R,3R,4R,5R,6S)-2-(((2S,4S,5S)-4,5-dihydroxytetrahydro-2H-pyran-2-yl)methoxy)-6-methyltetrahydro-2H-pyran-3,4,5-triol.

"Alkyl" means linear saturated monovalent radicals of one to eight carbon atoms or a branched saturated monovalent of three to eight carbon atoms. It may include hydrocarbon radicals of one to four or one to three carbon atoms, which may be linear. Examples include methyl, ethyl, propyl, 2-propyl, isopropyl, n-butyl, iso-butyl, tert-butyl, pentyl, and the like. In certain embodiments, the alkyl group is a linear or branched chain $C_1$ to $C_6$ alkyl group, $C_1$ to $C_5$ alkyl group, $C_1$ to $C_4$ alkyl group, $C_1$ to $C_3$ alkyl group, ethyl, or methyl group.

The term "hydrocarbon" or "hydrocarbyl" refers to organic compounds or radicals consisting exclusively of the elements carbon and hydrogen. Hydrocarbyl includes alkyl, alkenyl, and alkynyl moieties.

The term "acyl" means a radical —C(O)R wherein R is hydrogen, alkyl or cycloalkyl, or heterocycloalkyl. In one embodiment, the R group of the radical —C(O)R is a $C_1$ to $C_4$ alkyl. Examples of acyl groups include, but are not limited to, formyl, acetyl, and ethylcarbonyl.

The term "halo" means fluoro, chloro, bromo, and iodo.

The term "hydroxy" means the radical —OH.

The term "substituted," as used herein, refers to an embodiment wherein at least one hydrogen atom of a compound or chemical moiety is replaced with a second chemical moiety. Non-limiting examples of substituents are those found in the exemplary compounds and embodiments disclosed herein, as well as halogen; alkyl; alkenyl; alkynyl; hydroxy; alkoxyl; amino; haloalkyl (e.g., trifluoromethyl); and —COOH. All chemical groups disclosed herein can be substituted, unless it is specified otherwise. For example, "substituted" alkyl, alkenyl, or alkynyl moieties described herein are moieties that are substituted with a second chemical moiety such as a hydrocarbyl moiety, halo, alkoxy, and —COOH. Substituted alkyl groups include, but are not limited to, haloalkyl, hydroxyalkyl, carboxylalkyl, and aminoalkyl.

The term "haloalkyl" means alkyl substituted with one or more same or different halo atoms. Representative examples of haloalkyl groups include, but are not limited to, —$CH_2Cl$, —$CH_2Br$, —$CF_3$, —$CH_2CH_2Cl$, and —$CH_2CCl_3$.

The term "amino," as used herein, refers to —$NH_2$.

The term "alkylamino" means a radical —NHR or —$NR_2$ where each R is independently an alkyl group. In certain embodiments, the alkyl group of alkylamino is a $C_1$ to $C_4$ alkyl. Representative examples of alkylamino groups include, but are not limited to, methylamino, (1-methylethyl) amino, methylamino, dimethylamino, methylethylamino, and di(1-methylethyl)amino.

The term "hydroxyalkyl" means an alkyl radical as defined herein, substituted with one or more, preferably one, two or three hydroxy groups. In certain embodiments, hydroxyalkyl is a $C_1$ to $C_6$ alkyl, or preferably a $C_1$ to $C_4$ alkyl, substituted with one or more hydroxy groups. Representative examples of hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl, and 1-(hydroxymethyl)-2-hydroxyethyl.

The term "alkoxy," as used herein, refers to the radical —$OR_x$, wherein $R_x$ is a $C_1$ to $C_6$ alkyl group. In one embodiment, $R_x$ is a $C_1$ to $C_4$ alkyl group. Exemplary alkoxy groups include, but are not limited to, methoxy, ethoxy, and propoxy.

In certain embodiments, the present invention pertains to isolated or substantially pure compounds represented by formula I to formula IV. The term "substantially pure," as used herein, refers to more than 99% pure.

As used herein, "isolated" refers to compounds that have been removed from any environment in which they may exist in nature. For example, an isolated compound would not refer to the compound as it exists in plants from which the compound can be isolated. In preferred embodiments, the compounds of the present invention are at least 75% pure, preferably at least 90% pure, more preferably are more than 95% pure, and most preferably are more than 99% pure (substantially pure).

The present invention further embodies stereoisomers of the compounds. The term "stereoisomer" encompasses all enantiomerically/stereomerically pure and enantiomerically/stereomerically enriched compounds disclosed herein.

In one embodiment, the present invention pertains to enantiomeric forms of the compounds. The enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

The present invention also encompasses salts, solvates, hydrates, and polymorphs of the compounds of formula I to formula IV, and uses thereof.

In one embodiment, the compounds useful according to the present invention do not include the compounds disclosed in International Application No.: PCT/IB2010/003482, entitled "Materials and Methods for Prevention and Treatment of Viral Infections."

In one embodiment, the compounds of formula I to formula IV have anti-viral activity.

In another aspect, the present invention provides uses of the compounds of formula I to formula IV, and salts, solvates, hydrates, polymorphs thereof, as well as compositions comprising these compounds, for preventing and/or treating viral infection. In one embodiment, the method comprises administering, to a subject in need of such prevention and/or a treatment, an effective amount of a composition comprising a compound selected from formula I or formula IV, or a salt, solvate, hydrate, or polymorph thereof.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters.

The term "antiviral," as used herein, includes but is not limited to, preventing, inhibiting, suppressing, reducing, adversely impacting, and/or interfering with the growth, survival, replication, function, and/or dissemination of a virus.

The term "treatment" or any grammatical variation thereof (e.g., treat, treating, etc.), as used herein, includes but is not limited to, alleviating or ameliorating a symptom of a disease or condition, and/or reducing the severity of a disease or condition.

The term "prevention" or any grammatical variation thereof (e.g., prevent, preventing, etc.), as used herein, includes but is not limited to, delaying the onset of symptoms, preventing relapse to a disease, decreasing the number or frequency of relapse episodes, increasing latency between symptomatic episodes, or a combination thereof.

The term "effective amount," as used herein, refers to an amount that is capable of treating, ameliorating, or preventing a disease or condition or otherwise capable of producing an intended therapeutic effect.

In one embodiment, the compounds and compositions of the present invention are useful for preventing and/or treating infections caused by influenza viruses, including but not limited to, any of the subtypes of influenza A, influenza B, or influenza C.

In one embodiment, the subject compounds, pharmaceutical compositions, and therapeutic methods are useful for preventing and/or treating infections caused by influenza A viruses, including but not limited to, any of the strains of H1N1, H1N2, H1N3, H1N4, H1N5, H1N6, H1N7, H1N8, H1N9, H2N1, H2N2, H2N3, H2N4, H2N5, H2N6, H2N7, H2N8, H2N9, H3N1, H3N2, H3N3, H3N4, H3N5, H3N6, H3N7, H3N8, H3N9, H4N1, H5N2, H5N3, H5N4, H5N5, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N6, H7N7, H7N8, H7N9, H8N1, H8N2, H8N3, H8N4, H8N5, H8N6, H8N7, H8N8, H8N9, H9N1, H9N2, H9N3, H9N4, H9N5, H9N6, H9N7, H9N8, H9N9, H10N1, H10N2, H10N3, H10N4, H10N5, H10N6, H10N7, H10N8, H10N9, H11N1, H11N2, H11N3, H11N4, H11N5, H11N6, H11N7, H11N8, H11N9, H12N1, H12N2, H12N3, H12N4, H12N5, H12N6, H12N7, H12N8, H12N9, H13N1, H13N2, H13N3, H13N4, H13N5, H13N6, H13N7, H13N8, H13N9, H14N1, H14N2, H14N3, H14N4, H14N5, H14N6, H14N7, H14N8, H14N9, H15N1, H15N2, H15N3, H15N4, H15N5, H15N6, H1N7, H15N8, and H15N9.

In another specific embodiment, the compounds and compositions of the present invention are useful for preventing and/or treating infections caused by influenza A viruses, including but not limited to, H1N1 (A/HK/54/98, oseltamivir-sensitive strain), H1N1 (A/Vicotria/07159200/07, oseltamivir-resistant strain), H9N2 (A/Quail/HK/G1/97), H3N2 (A/H3N2/1174/99), H5N1 (A/H5N1/97), H1N1 (A/54/98), H9N2/G1, and H6N1 (A/Teal/HK/W312/97).

In another specific embodiment, the compounds and compositions of the present invention are useful for preventing and/or treating infections caused by viruses, including but not limited to, respiratory syncytial virus, rhinovirus, HIV virus; hepatitis viruses including hepatitis A virus, hepatitis B virus, hepatitis C virus, hepatitis D virus, hepatitis E virus, hepatitis F virus, and hepatitis G virus; oncoviruses; human papilloma virus (HPV); human T-lymphotropic virus Type I (HTLV-1); bovine leukemia virus (BLV); Epstein-Barr virus; herpes simplex virus 1; herpes simplex virus 2; coronavirus; and poliovirus.

In addition, the compounds and compositions of the present invention are useful for preventing and/or treating infections caused by pathogens, including but not limited to, bacteria, fungi, parasitic microorganisms, and protozoan.

In one embodiment, the compounds and compositions of the present invention are useful for treating fever in a subject.

The present invention also provides for a therapeutic method by administering therapeutic or pharmaceutical compositions in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions.

Suitable methods of administration include, but are not limited to, oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

In one embodiment, the subject method further comprises administering to a subject a second anti-viral agent, including but not limited to, compounds such as adamantanes and neuraminidase inhibitors, zanamivir, oseltamivir, peramivir, and seltamivir; interferons; nucleotides; siRNAs; or any of the combination thereof; and wherein the second antiviral agent can be administered prior to, subsequent to, or simultaneous with the compounds or pharmaceutical compositions of the subject invention.

In a specific embodiment, the subject method further comprises administering to a subject a second anti-viral agent, selected from the group consisting of zanamivir, oseltamivir, peramivir, seltamivir, and any of the combination thereof; wherein the second antiviral agent can be administered prior to, subsequent to, or simultaneous with the compounds or pharmaceutical compositions of the subject invention.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In one embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include, but are not limited to, sodium, potassium, magnesium, ammonium, calcium, ferric hydroxides, isopropylamine, triethylamine, 2-ethylamino ethanol, histidine, procaine, acetate, aspartate, citrate, fumarate, hippurate, hydrochloride, lactate salt, malate salt, phosphate, sulfate, hemi-sulfate, tartrate, gluconate, maleate, and succinate salt.

The present invention also provides for the modification of the compound such that it is more stable once administered to a subject, i.e., once administered it has a longer time period of effectiveness as compared to the unmodified compound. Such modifications are well known to those of skill in the art, e.g., microencapsulation, etc.

The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 2 mg/kg. In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective mg/kg dose for humans based on data generated from rat studies, the effective mg/kg dosage in rats is divided by six.

The invention also provides a pharmaceutical pack or kit comprising one or more containers filled with one or more of the ingredients, e.g., compound, carrier suitable for administration.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A method for treating a viral infection, comprising administering, to a subject in need of such treatment, an effective amount of a compound selected from:

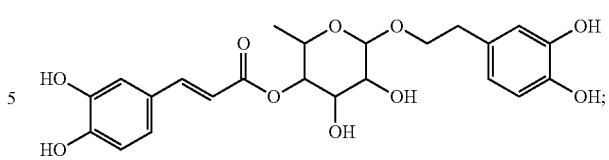

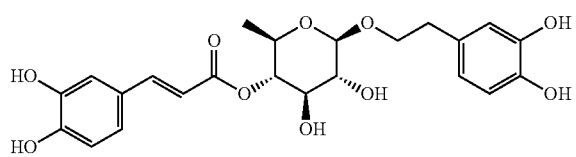 [SMILES: C[C@H]1O[C@@H](OCCc2ccc(O)c(O)c2)[C@H](O)[C@@H](O)[C@@H]1OC(=O)/C=C/c1ccc(O)c(O)c1]

(E)-(2R,3S,4R,5R,6R)-6-(3,4-dihydroxyphenethoxy)-4,5-dihydroxy-2-methyltetrahydro-2H-pyran-3-yl 3-(3,4-dihydroxyphenyl)acrylate;

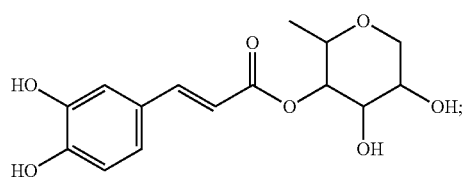 [SMILES: CC1OCC(O)C(O)C1OC(=O)/C=C/c1ccc(O)c(O)c1]

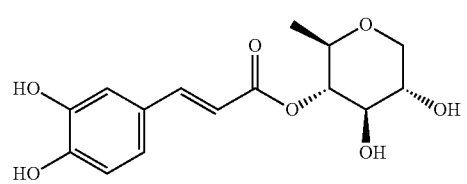 [SMILES: C[C@H]1OC[C@H](O)[C@@H](O)[C@@H]1OC(=O)/C=C/c1ccc(O)c(O)c1]

(E)-(2R,3S,4R,5S)-4,5-dihydroxy-2-methyltetrahydro-2H-pyran-3-yl 3-(3,4-dihydroxyphenyl)acrylate;

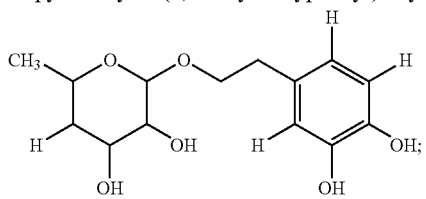

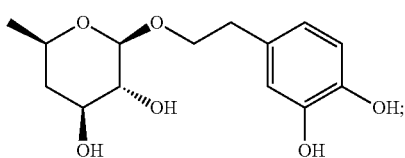 [SMILES: C[C@@H]1C[C@H](O)[C@@H](O)[C@H](OCCc2ccc(O)c(O)c2)O1]

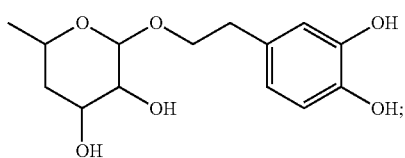 [SMILES: CC1CC(O)C(O)C(OCCc2ccc(O)c(O)c2)O1]

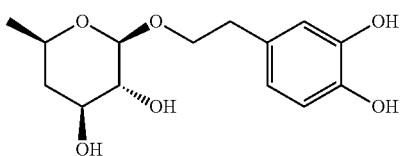 [SMILES: C[C@@H]1C[C@H](O)[C@@H](O)[C@H](OCCc2ccc(O)c(O)c2)O1]
(2R,3R,4S,6R)-2-(3,4-dihydroxyphenethoxy)-6-methyltetrahydro-2H-pyran-3,4-diol;
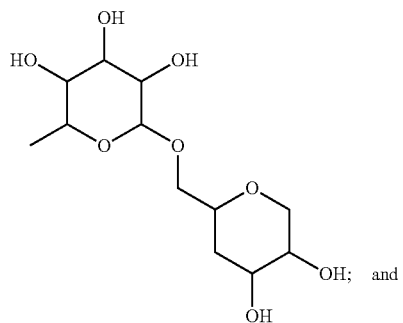 [SMILES: CC1OC(OCC2CC(O)C(O)CO2)C(O)C(O)C1O ; "and"]
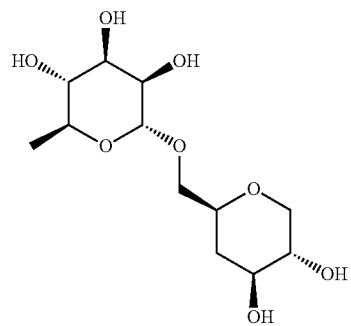 [SMILES: C[C@@H]1O[C@@H](OC[C@@H]2C[C@H](O)[C@@H](O)CO2)[C@H](O)[C@H](O)[C@H]1O]
(2R,3R,4R,5R,6S)-2-(((2S,4S,5S)-4,5-dihydroxytetrahydro-2H-pyran-2-yl)methoxy)-6-methyltetrahydro-2H-pyran-3,4,5-triol;
including salts thereof.
2. The method of claim 1, used to treat an influenza virus infection.
* * * * *

UNITED STATES PATENT AND TRADEMARK OFFICE
CERTIFICATE OF CORRECTION

PATENT NO.        : 9,156,871 B2
APPLICATION NO.   : 13/863781
DATED             : October 13, 2015
INVENTOR(S)       : Allan Sik Yin Lau and Lai Hung Cindy Yang It is certified that error appears in the above-identified patent and that said Letters Patent is hereby corrected as shown below:

In the Specification

Column 4,

Line 58 " 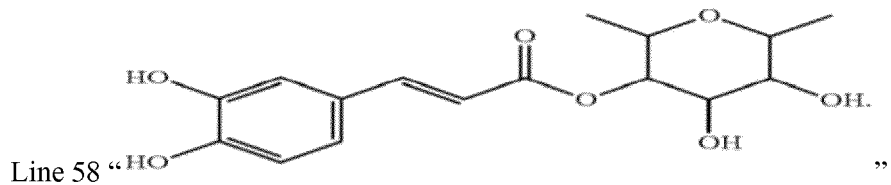 "

Should read

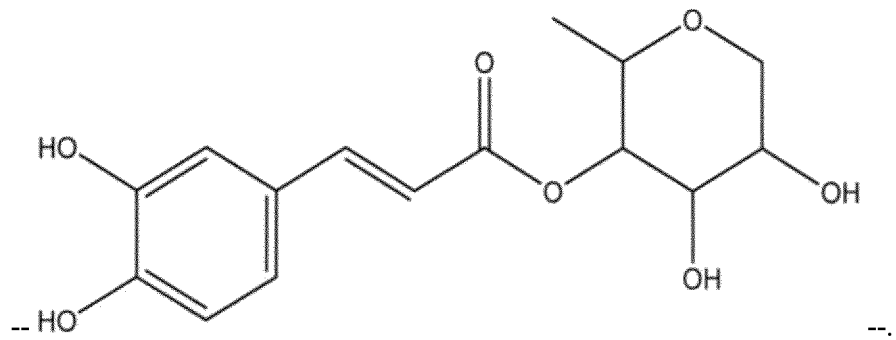 --.

Signed and Sealed this
Nineteenth Day of April, 2016

Michelle K. Lee
*Director of the United States Patent and Trademark Office*